US00PP33371P2

(12) United States Plant Patent
Van Swieten

(10) Patent No.: US PP33,371 P2
(45) Date of Patent: Aug. 17, 2021

(54) ***PHALAENOPSIS* ORCHID PLANT NAMED 'PHALHAISWE'**

(50) Latin Name: ***Phalaenopsis* hybrid**
Varietal Denomination: PHALHAISWE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,109

(22) Filed: Mar. 10, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *phalaenopsis* plant named, 'PHALHAISWE', QZ PBR 2019/2389, application date Sep. 23, 2019.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALHAISWE', particularly characterized by purplish-pink flowers with light purple and light reddish-purple lips, a flat flower shape in lateral view, a concave dorsal sepal shape in cross section, and is propagated by meristem tissue culture, is disclosed.

3 Drawing Sheets

Genus and species: *Phalaenopsis* hybrid.
Variety denomination: 'PHALHAISWE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHAISWE'.

The new *Phalaenopsis* plant is a product of a planned breeding program conducted by the inventor in Bleiswijk, the Netherlands. The objective of this breeding program was to create a new *Phalaenopsis* plant with numerous attractive purplish-pink flowers with light purple and light reddish-purple lips, suitable for potted plant production.

The new *Phalaenopsis* plant 'PHALHAISWE' is a result of cross-pollination made by the inventor in November 2011 in Bleiswijk, the Netherlands, of the proprietary female, or seed parent, *Phalaenopsis* hybrid '35337-01' (unpatented) with the proprietary male, or pollen parent, *Phalaenopsis* hybrid 'PHALVAPYH' (U.S. Plant Pat. No. 31,052).

The new *Phalaenopsis* was selected by the inventor as a single plant within the progeny of the stated cross-pollination in a controlled greenhouse in Bleiswijk, the Netherlands, in August 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019 (Application no. 2019/2389), by Applicant who obtained the subject matter disclosed directly from the inventor. 'PHALHAISWE' has not been made publicly available or sold anywhere in the world prior to the effective filing date of this application with the exception of sales or disclosures made one year or less before the effective filing date of this claimed invention by Applicant who obtained 'PHALHAISWE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHAISWE' as a new and distinct variety of *Phalaenopsis* plant:

1) Purplish-pink flowers with light purple and light reddish-purple lips;
2) Flower shape in lateral view is flat; and
3) Dorsal sepal shape in cross section is concave.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in January 2021. Colors in the photographs may differ from the color values cited in the detailed botanical description, which accurately describe the actual colors of the new variety.

DESCRIPTION OF THE NEW VARIETY

Figure 1:
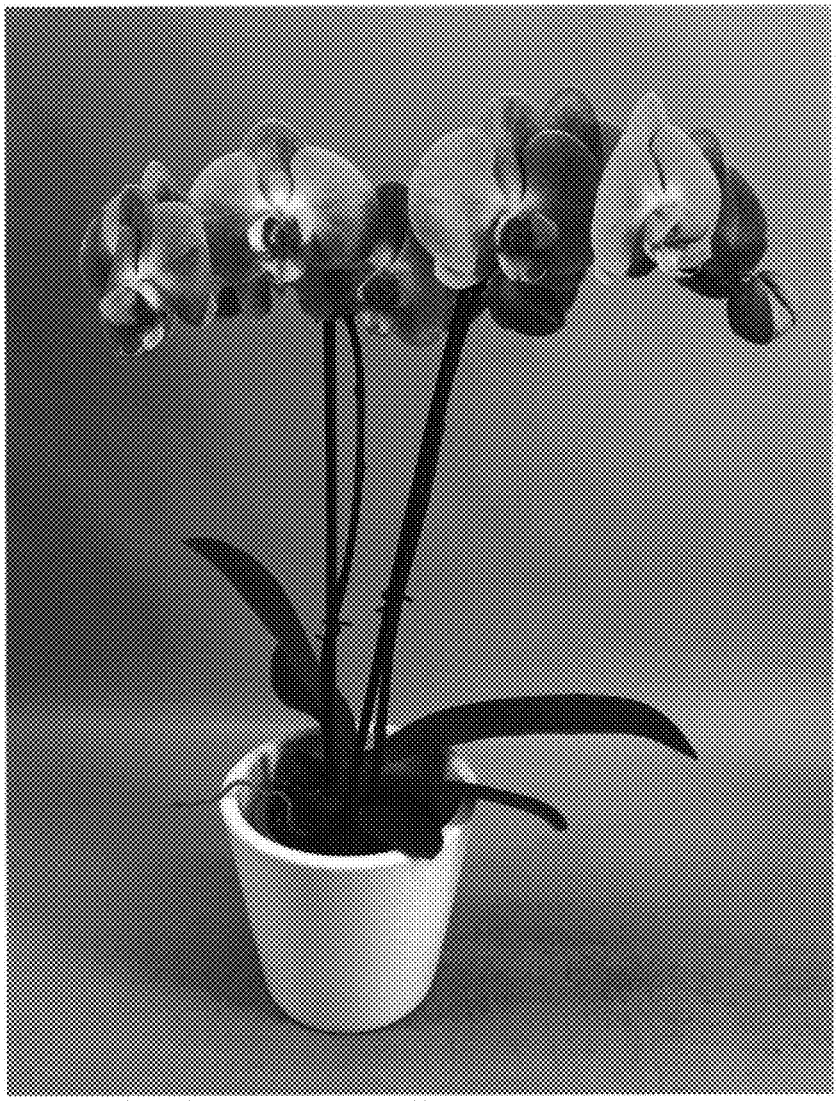
FIG. 1 shows the overall plant habit, including blooms, buds, and foliage of 'PHALHAISWE'.
Figure 2:
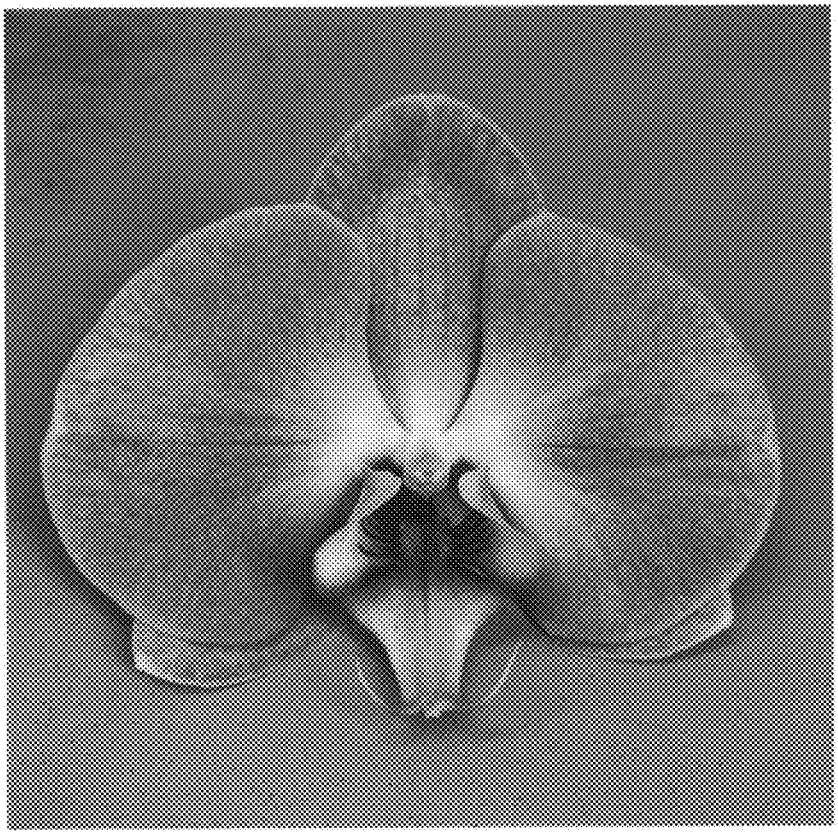
FIG. 2 shows a close-up of a flower of 'PHALHAISWE'.
Figure 3:
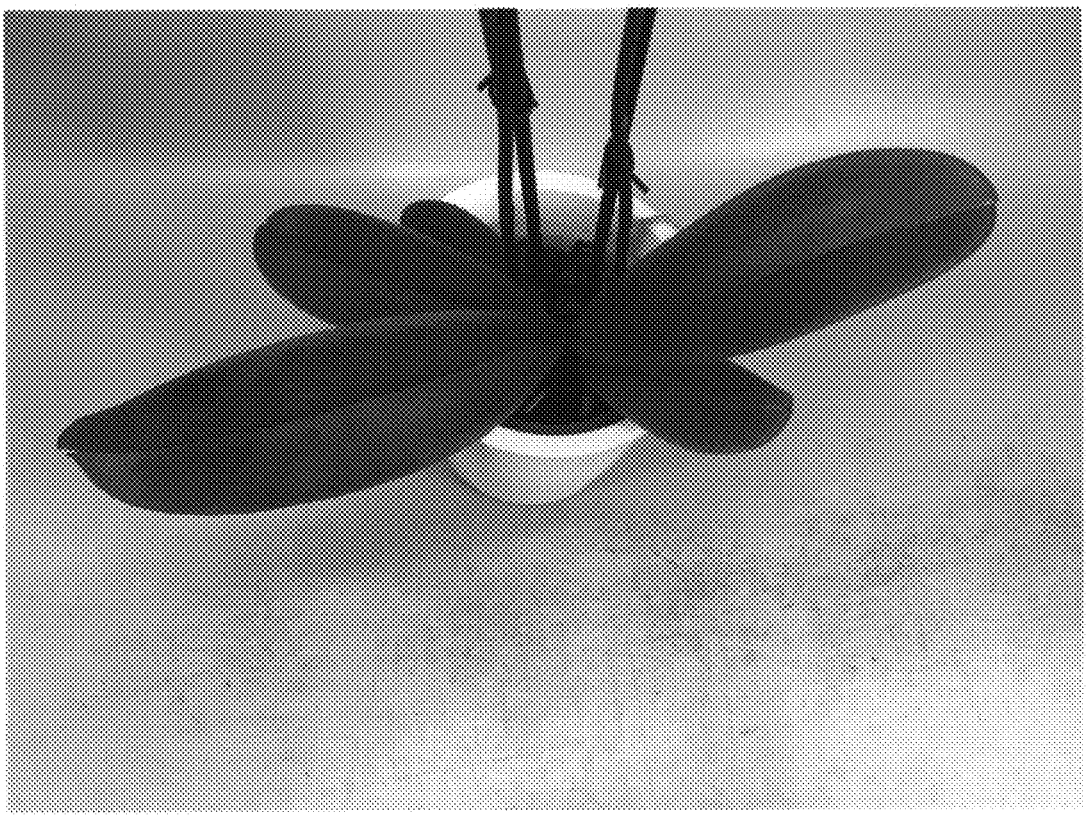
FIG. 3 shows an overhead view of the leaves of 'PHALHAISWE'.

The following detailed description sets forth the distinctive characteristics of 'PHALHAISWE'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in January 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALHAISWE'.

Parentage:

*Female parent.*—*Phalaenopsis* cultivar '35337-01' (unpatented).

*Male parent.*—*Phalaenopsis* cultivar 'PHALVAPYH' (U.S. Plant Pat. No. 31,052).

Propagation:

*Type.*—Meristem tissue culture.

Roots:

*Root description.*—Greyed-green (a color in between RHS 190B and RHS 190C) colored roots with branching lateral roots having yellow-green (RHS N144D) colored root tips with a touch of purplish-red (RHS N77B).

Plant:

*Crop time to flowering.*—Following asexual propagation (in vitro), the rooted cuttings grow for 20-24 weeks. After transplantation into 12-cm pots, the plants are finished after 48 to 50 weeks.

*Growth habit of the peduncle.*—Upright to slightly pendent with raceme inflorescence.

*Height (from soil level to top of inflorescence).*—Approximately 45.0 cm to 50.0 cm.

*Width (measured from leaf tips).*—About 33.0 cm to 36.0 cm.

*Vigor.*—Moderate.

Leaves:

*Mature leaves.*—Quantity per plant: 6 to 8 leaves are produced before flowering. Length (fully expanded): 21.0 cm to 24.0 cm. Width: 6.0 cm to 7.0 cm. Shape: Oblong. Base shape: Moderately to very elongated. Apex: Acute unequal. Leaf blade angle with the petiole (measured from the horizontal position): Between 20 degrees and 35 degrees. Leaf margin: Entire. Color: Upper surface: RHS 146A and diluting reddish-brown margin (RHS 200B) toward the tip. Lower surface: RHS 146B and diluting dark red-brown region and margin (a color in between RHS 187A and RHS 200B) toward the tip. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B with a touch of diluting dark red (RHS 187A) toward the tip.

Peduncle:

*Quantity per plant.*—1 to 2.

*Number of flowers per peduncle.*—6 to 8.

*Length.*—45.0 cm to 50.0 cm.

*Diameter.*—5.0 mm to 6.0 mm.

*Strength.*—Strong.

*Aspect.*—Upright to slightly pendent.

*Texture.*—Smooth.

*Color.*—Dark reddish-brown (a color in between RHS 200A and RHS 187A) with a touch of yellow-green (RHS 146C).

*Internode length.*—3.0 cm to 4.0 cm.

Inflorescence description:

*Appearance.*—Upright to slightly pendent, raceme inflorescence with bilaterally symmetrical flowers that open in succession beginning with the lowermost flower.

*Number of inflorescences.*—1 to 2.

*Inflorescence size.*—Height (from base to tip): 130.0 mm to 160.0 mm.

*Flowering time.*—First flowers can be expected 10 to 11 months after planting in a 12-cm pot.

*Flower.*—Height: 83.0 mm to 88.0 mm. Diameter: 105.0 mm to 110.0 mm. Depth of lip: 33.0 mm to 35.0 mm.

*Flower longevity.*—On the plant: 12 to 14 weeks.

*Flower shape.*—Flat.

*Fragrance.*—Absent.

*Flower bud.*—Average size: Medium to large. Length: 27.0 mm to 29.0 mm. Width: 24.0 mm to 26.0 mm. Shape: Egg shaped. Color: Purplish-red (a color in between RHS N77B and RHS N79C).

*Petals.*—Arrangement: Open/free. Shape: Semi-circular. Apex: Emarginated asymmetric. Margin: Moderately undulated. Length (from base to tip): 49.0 mm to 51.0 mm. Width: 65.0 mm to 67.0 mm. Position of the broadest part of the petal: At the base. Color (when fully opened): Upper surface: Basic color: Purplish-pink (RHS N78C). Over color: White (RHS NN155C) at the base. Lower surface: Basic color: Light purple (RHS 76A); diluting purplish-pink stripes (RHS N78C). Over color: Light reddish-purple (RHS N78D) toward margin. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal.*—Shape: Elliptic. Apex: Emarginated symmetric. Margin: Entire. Length (from base to tip): 50.0 mm to 52.0 mm. Width: 39.0 mm to 41.0 mm. Color (when fully opened): Upper surface: Basic color: Light reddish-purple (RHS N78D). Over color: White (RHS NN155C) at the base; purplish-pink shade (RHS N78C); diluting stripes (RHS N78C). Lower surface: Basic color: Light reddish-purple (RHS N78D). Over color: Light yellow-green (RHS 145C). Number of spots and stripes on the dorsal sepals (upper surface): Few to medium stripes. Color of spots and stripes on the dorsal sepals (upper surface): RHS N78C. Density of netting of the dorsal sepals (upper surface): Low. Color of the netting (upper surface): RHS N78C.

*Lateral sepals.*—Shape: Ovate. Apex: Obtuse asymmetric. Margin: Entire. Length (from base to tip): 52.0 mm to 54.0 mm. Width: 34.0 mm to 36.0 mm. Color (when fully opened): Upper surface: Basic color: Light purple (RHS 76A). Over color: Light yellow-green (a color in between RHS. 145C and RHS 145D) with a small red region (RHS 185C) at the base; diluting stripes (a color in between RHS N78C and RHS N78D) and light reddish-purple (RHS N78D) toward margin. Lower surface: Basic color: Purplish-pink (RHS N78C). Over color: Light yellow-green (RHS 145D); reddish-purple stripes (RHS N78B). Number of spots, dots, and stripes on the lateral sepals (upper surface): Medium stripes. Color of spots, dots, and stripes on the lateral sepals (upper surface): RHS N78D. Density of netting of the lateral sepals (upper surface): None. Color of the netting (upper surface): Not applicable.

*Labellum* (*lip*).—Whiskers: Present. Length of whiskers: 10.0 mm to 12.0 mm. Color of whiskers: Purplish-pink (RHS N78C) with white tips (RHS NN155C). Pubescence on the lip: Absent.

*Lateral lobe.*—Shape: Type V (as described in the International Union for the Protection of New Varieties of Plants (UPOV) Test Guidelines for *Phalaenopsis*); spatulate. Margin: Undulated (widely wavy). Length: 23.0 mm to 25.0 mm. Width: 17.0 mm to 19.0 mm. Color: Upper surface: White (RHS NN155C); striped (RHS 59B) at the base; yellow (RHS 13B) with reddish-orange margin (RHS 175B) on one side; purplish-pink shade (RHS N78C). Lower surface: White (RHS NN155A); yellow (RHS 13B) with reddish-orange margin (RHS 175B) on one side; purplish-pink shade (RHS N78C). Number of spots and stripes on the lateral lobe (upper surface): Few to medium stripes at the base. Color of spots and stripes on the lateral lobe (upper surface): RHS 59B. Density of netting of the lateral lobe (upper surface): None. Color of the netting (upper surface): Not applicable.

*Apical lobe.*—Shape: Triangular. Margin: Entire. Length: 23.0 mm to 25.0 mm. Width: 25.0 mm to 27.0 mm. Color: Upper surface: Red margin (RHS 184B) and yellow (RHS 13C) at the base; light purple (RHS 76A) and light reddish-purple (RHS N78D) toward whiskers. Lower surface: Red margin (RHS 184B) at the base; yellow wings (RHS 13C); light reddish-purple (RHS N78D) and purplish-pink (RHS N78C) toward whiskers. Number of spots and stripes on the apical lobe (upper surface): None. Color of spots and stripes on the apical lobe (upper surface): Not applicable. Density of netting of the apical lobe (upper surface): None. Color of the netting (upper surface): Not applicable. Bump and ridge: Present.

*Callus.*—Average size: Medium to large. Height: 7.0 mm to 8.0 mm. Length: 6.0 mm to 7.0 mm. Width: 4.0 mm to 5.0 mm. Color: Yellow (RHS 14A) toward the tip and light greenish-yellow (RHS 8C) on sides; dotted (RHS 183C).

Reproductive organs:

*Column.*—Length: 9.0 mm to 11.0 mm. Diameter: 5.8 mm to 6.3 mm. Color: Very light purple (RHS 76B) with light reddish-purple tip (RHS N78D).

*Pollinia.*—Quantity: 2. Diameter: 0.9 mm to 1.1 mm. Color: Orange (RHS 24A).

*Ovary.*—Length: 10.0 mm to 12 0 mm. Diameter: 2.3 mm to 2.6 mm.

*Pedicel.*—Length: 35.0 mm to 37.0 mm. Diameter: 2.7 mm to 3.0 mm. Color: Yellow-green (RHS 147C) with a touch of purplish-red (RHS N77B) at the base; lighter yellow-green (RHS 195B) and light purplish-red (RHS N78D) toward flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHAISWE' differs from the female parent plant '35337-01' (unpatented) in that 'PHALHAISWE' has purplish-pink whiskers with white tips and a medium curvature of the lateral lobe, whereas '35337-01' has light purple whiskers and a weak curvature of the lateral lobe. Additionally, 'PHALHAISWE' has larger flowers than '35337-01'.

'PHALHAISWE' differs from the male parent plant 'PHALVAPYH' (U.S. Plant Pat. No. 31,052) in that 'PHALHAISWE' has purplish-pink whiskers with white tips and a medium curvature of the lateral lobe, whereas 'PHALVAPYH' has reddish-purple whiskers and a weak curvature of the lateral lobe. Additionally, 'PHALHAISWE' has larger flowers than 'PHALVAPYH'.

'PHALHAISWE' is most similar to the commercial *Phalaenopsis* plants named 'PHALHAKAK' (U.S. Plant patent application Ser. No. 16/974,412) and 'PHALARALS' (U.S. Plant Pat. No. 38,097). 'PHALHAISWE' differs from the commercial variety 'PHALHAKAK' in that 'PHALHAISWE' has emarginated dorsal sepal apexes, whereas 'PHALHAKAK' has obtuse dorsal sepal apexes. Additionally, 'PHALHAISWE' has a shorter plant, shorter whiskers, and longer leaves than 'PHALHAKAK'.

'PHALHAISWE' differs from the commercial variety 'PHALARALS' in that 'PHALHAISWE' has very light purple columns with light reddish-purple tips, whereas 'PHALARALS' has white columns with very light purple tips. Additionally, 'PHALHAISWE' has shorter whiskers and longer leaves than 'PHALARALS'.

I claim:

1. A new and distinct variety of *Phalaenopsis* plant named 'PHALHAISWE', substantially as described and illustrated herein.

* * * * *